United States Patent
Lim et al.

(10) Patent No.: US 8,932,338 B2
(45) Date of Patent: Jan. 13, 2015

(54) NONINVASIVE METHOD FOR SITE-SPECIFIC FAT REDUCTION

(75) Inventors: Susan M. L. Lim, Singapore (SG); Steven C. Shanks, Mesa, AZ (US); Rodrigo Neira, Toronto (CA)

(73) Assignee: Erchonia Corporation, McKinney, TX (US)

(*) Notice: Subject to any disclaimer, the term of this patent is extended or adjusted under 35 U.S.C. 154(b) by 2126 days.

(21) Appl. No.: 11/053,369

(22) Filed: Feb. 7, 2005

(65) Prior Publication Data
US 2005/0203594 A1 Sep. 15, 2005

Related U.S. Application Data

(60) Provisional application No. 60/542,720, filed on Feb. 6, 2004.

(51) Int. Cl.
| | |
|---|---|
| A61N 5/06 | (2006.01) |
| A61B 18/18 | (2006.01) |
| C02F 1/00 | (2006.01) |
| C02F 1/32 | (2006.01) |
| C02F 9/00 | (2006.01) |
| F03B 1/00 | (2006.01) |
| F03B 13/00 | (2006.01) |
| H02K 7/18 | (2006.01) |

(Continued)

(52) U.S. Cl.
CPC ............ *A61N 5/0613* (2013.01); *C02F 1/008* (2013.01); *C02F 1/325* (2013.01); *C02F 9/005* (2013.01); *F03B 1/00* (2013.01); *F03B 13/00* (2013.01); *H02K 7/1823* (2013.01); *A61N 2005/0644* (2013.01); *A61N 2005/0651* (2013.01); *A61N 2005/067* (2013.01); *Y02B 10/50* (2013.01); *Y02E 10/223* (2013.01); *C02F 1/001* (2013.01); *C02F 1/283* (2013.01); *C02F 1/32* (2013.01); *C02F 2201/009* (2013.01); *C02F 2201/3222* (2013.01); *C02F 2201/326* (2013.01); *C02F 2209/005* (2013.01); *C02F 2209/006* (2013.01); *C02F 2307/06* (2013.01); *F05B 2220/602* (2013.01); *F05B 2240/2411* (2013.01)
USPC ................... 607/89; 606/3; 606/10; 606/13

(58) Field of Classification Search
USPC .......................................... 606/9; 607/88–91
See application file for complete search history.

(56) References Cited

U.S. PATENT DOCUMENTS

| | | |
|---|---|---|
| 5,143,063 A | 9/1992 | Fellner |
| 5,507,790 A | 4/1996 | Weiss |
| 5,725,482 A | 3/1998 | Bishop |

(Continued)

OTHER PUBLICATIONS

Neira, et. al, "Fat Liquefaction: Effect of Low-Level Laser Energy on Adipose Tissue," Plastic and Reconstructive Surgery (2002), 110(3):912-922.

(Continued)

*Primary Examiner* — Linda Dvorak
*Assistant Examiner* — Adam Avigan
(74) *Attorney, Agent, or Firm* — Etherton Law Group, LLC

(57) ABSTRACT

A noninvasive method of reducing fat from targeted regions of a patient's body by applying low-level laser energy externally through the skin of the patient to the targeted areas. Sufficient laser energy is applied to release at least a portion of intracellular fat into the interstitial space. The released intracellular fat is removed from the body through the body's natural functions. The preferred embodiment uses laser energy at about 635 nm.

10 Claims, 2 Drawing Sheets

(51) Int. Cl.
*A61N 5/067* (2006.01)
*C02F 1/28* (2006.01)

(56) References Cited

U.S. PATENT DOCUMENTS

| | | | |
|---|---|---|---|
| 6,013,096 A | 1/2000 | Tucek | |
| 6,106,516 A | 8/2000 | Massengil | |
| 6,235,016 B1 | 5/2001 | Stewart | |
| 6,328,733 B1 | 12/2001 | Trost | |
| 6,475,211 B2 | 11/2002 | Chess et al. | |
| 6,517,532 B1 | 2/2003 | Altshuler et al. | |
| 6,605,079 B2 | 8/2003 | Shanks | |
| 6,645,162 B2 | 11/2003 | Friedman | |
| 6,673,096 B2 | 1/2004 | Lach | |
| 6,676,655 B2 * | 1/2004 | McDaniel | 606/9 |
| 6,746,473 B2 | 6/2004 | Shanks | |
| 7,101,385 B2 * | 9/2006 | Shellman | 607/88 |
| 7,309,335 B2 * | 12/2007 | Altshuler et al. | 606/11 |
| 2003/0069617 A1 | 4/2003 | Boutoussov et al. | |
| 2003/0083536 A1 | 5/2003 | Eshel | |
| 2004/0093047 A1 | 5/2004 | Lach | |
| 2004/0111132 A1 * | 6/2004 | Shenderova et al. | 607/88 |
| 2004/0147984 A1 | 7/2004 | Altshuler et al. | |
| 2004/0191278 A1 | 9/2004 | Christensen | |
| 2004/0210214 A1 | 10/2004 | Knowlton | |
| 2004/0236252 A1 | 11/2004 | Muzzi et al. | |
| 2005/0197681 A1 | 9/2005 | Barolet | |

OTHER PUBLICATIONS

Brown, Spencer et al, Discussion of "Fat Liquefaction: Effect of Low-Level Laser Energy on Adipose Tissue," Plastic and Reconstructive Surgery (2002), 110(3):923.

* cited by examiner

NONINVASIVE METHOD FOR SITE-SPECIFIC FAT REDUCTION

CROSS-REFERENCE TO RELATED APPLICATIONS

This application claims the benefit of U.S. Provisional Application No. 60/542,720 filed Feb. 6, 2004.

FIELD OF INVENTION

This invention relates to a method for non-invasive, non-traumatic shaping and contouring of a human body by external means. In particular, this invention relates to the application of laser energy to targeted external regions of a patient's body to reduce fat by facilitating the removal of the intracellular fat from fat cells in the targeted areas.

BACKGROUND

There is a great demand to be slimmer. Many people resort to the cosmetic surgical procedure known as liposuction, wherein excess adipose tissue, also known as fat, is suctioned from the body of a patient. The typical purpose of the liposuction procedure is to leave the patient thinner, with aesthetically more appealing body contours. For example, liposuction is often performed on patients to remove excess fat in the abdominal, buttock, thigh, breast and arm regions of the body.

Adipose tissue is made of adipocytes, or fat cells, which are enclosed membranes filled with globules of triglycerides. In normal fat the fat cells have regular contours and form into grapelike clusters. The intracellular fat is relatively fluid and, if the membrane is pierced, will flow out of the cell into the interstitial space. The interstitial space includes nerves, blood vessels, lymphatics and collagen fibers, among other substances.

Liposuction is performed by inserting a narrow tube, or cannula, through a tiny incision in the skin into the subcutaneous fatty tissue. The cannula is repeatedly pushed then pulled through the fat layer, separating and puncturing the fat cells and suctioning them out. Suction action through the cannula is provided by a vacuum pump or a large syringe. The procedure carries with it some risks and side effects. Due to the physical damage induced, the procedure can damage nerves, lymphatics and vasculature in the surrounding area, often resulting in significant loss of blood as the blood is vacuumed out with the fat and the formation of seroma due to damaged lymphatic channels. In addition, the post-procedure recovery period is long and often accompanied by a great deal of inflammation, bruising and concomitant pain.

Since the liposuction technique was first developed there have been many improvements to the technique, with the goal of making the surgery less dangerous for the patient, as well as reducing the negative aspects of the post-operative recovery period. For example, in the tumescent technique known in prior art, a saline solution containing very dilute amounts of at least an anesthetic and a vasoconstrictor is injected subcutaneously into the area to be suctioned. The anesthetic reduces operative and post-operative pain and the vasoconstrictor helps reduce blood loss. Cannulas have been improved by enabling the cannula to emit laser light and ultrasound energy directly onto the fat cells. This internal application of energy melts the cell wall, releasing the intracellular fat, thereby making the fatty tissue less viscous and more easily suctioned up through the narrow cannula. These procedures suffer the disadvantage of still having to physically stab the cannula repeatedly in the fat layer as well as essentially melting the adipose tissue, resulting in undesirable levels of bruising, inflammation, pain, blood loss, and seroma formation. Recovery time is significant.

In U.S. Pat. No. 6,605,079, issued to one of the inventors of this method and incorporated herein, a less-destructive method is disclosed that uses low energy laser therapy in conjunction with suction of the fat cells. Low level laser therapy (LLLT) has been used increasingly in the treatment of a broad range of conditions such as treatment and repair of injured muscles and tendons. LLLT has improved wound healing, reduced edema, and relieved pain of various etiologies. LLLT has been used successfully post-operative to liposuction to reduce inflammation and pain. While a significant improvement over prior art, it is still invasive and carries with it the corresponding pain and risks.

Non-invasive methods of fat reduction are preferred over invasive methods to minimize trauma to the patient, reduce the risk of infection, and speed up recovery time, among other reasons. To that end, topical agents have long been known which claim to reduce cellulite or at least the appearance of cellulite. The effect of these agents on cellulite is somewhat dubious, and these agents are not known to actually reduce fat. Some of the topical agents are used in combination with massage or radiation of the affected areas.

To avoid invasive procedures, electromagnetic energy, such as microwave, ultrasound or radio frequency radiation, has also been used to reduce fat. In U.S. Pat. No. 5,507,790 issued to Weiss, a method is described in which a medicament is applied to a patient's skin where fat removal is desired and focused electromagnetic energy is applied to the same work site to heat the fatty tissue and increase fat lipolysis. In U.S. Pat. No. 5,143,063, Fellner takes this method even farther, applying sufficient electromagnetic radiation to destroy the fat cells. Yet another method is to inject an intumescing solution below the skin and apply electromagnetic energy externally to the body. These procedures are disadvantageous in that they utilize such high energy sources that they excessively heat the surrounding tissue, which can result in damage to the tissue and pain. Again, recovery time is significant.

Other external applications of certain types of destructive energy is known in the art. U.S. Pat. No. 6,645,162 issued to Friedman, et al. discloses the superposition of ultrasound waves from two or more sources to create a wave having high intensity localized at the adipose tissue to be treated. With this method, fat cells are sonically disintegrated, allowing the body to dispose of the fat that has been freed. In addition to destruction of cells, another difficulty with this method is accurately obtaining the desired focal zone under the skin.

It is desirable to remove fat with less damage to the fatty tissue, less blood loss, less post-operative bruising, inflammation, and pain than existing methods. Therefore, an object of this invention is to provide a non-invasive method of reducing fat. Another object is to provide a non-invasive method of reducing fat that does not destroy the fat cells, or damage surrounding tissue or structures. It is another object to eliminate the need for recovery time.

SUMMARY OF THE INVENTION

This invention is a noninvasive method of reducing fat from targeted regions of a patient's body by applying low-level laser energy externally through the skin of the patient to the targeted areas. Sufficient laser energy is applied to release at least a portion of intracellular fat into the interstitial space. The released intracellular fat is removed from the body through the body's natural functions. The preferred embodiment uses laser light at about 635 nm.

DETAILED DESCRIPTION OF THE INVENTION

Figure 1:
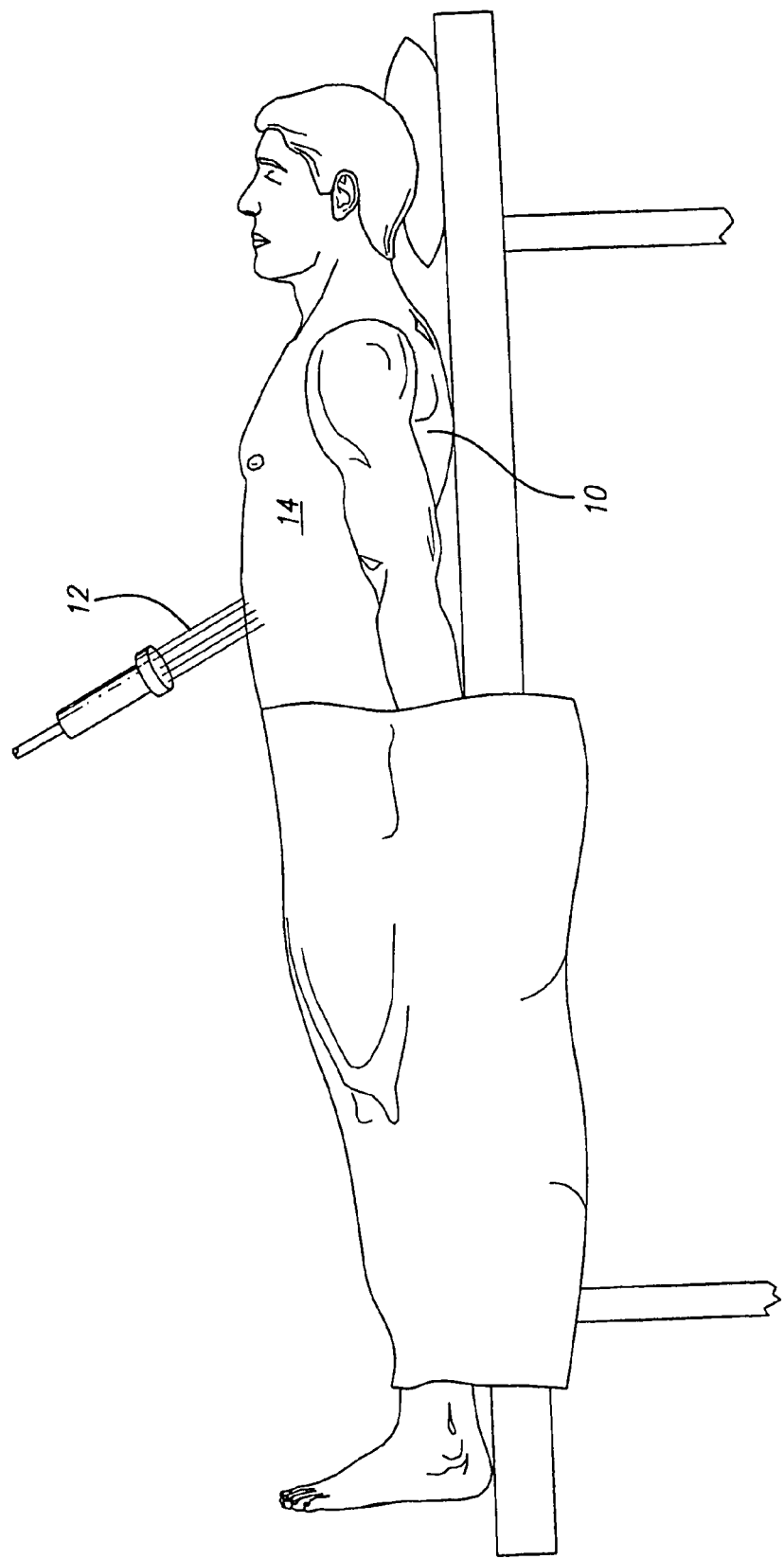
FIG. 1 Schematic illustration of application of low-level laser radiation.

This invention is a method for removing adipose tissue from a patient's body 10. As illustrated in FIG. 1, laser energy 12 is applied to the adipocyte tissue externally through the skin 14 of the patient. Sufficient laser energy is applied to release at least a portion of the intracellular fat 23 into the interstitial space 32. The released intracellular fat is removed from the body through the body's normal systems, such as metabolic, lymphatic or excretory systems. The procedure may be repeated in one or more additional areas to remove additional fat there. In that event, additional laser energy would be applied externally to the new area.

Typically, fat leakage into the interstitial space is seen as early as 3-5 minutes of laser energy application. This leakage continues for treatments as long as about 12-15 minutes with no fat cell destruction. However, at treatments of over about 12 minutes, fat cells start being destroyed. Therefore, the preferred method of treatment is to apply repeated treatments of less than 12 minutes each. Conversely, for patients with more fat to treat, it may be desirable to destroy the fat cells so that it cannot recover and reaccumulate fat. In such case, sufficient laser energy is applied to destroy fat cells without heating them or surrounding tissue. That is, for destructive treatments, each treatment will be at least 12 minutes and preferably 15-20 minutes.

Figure 2:
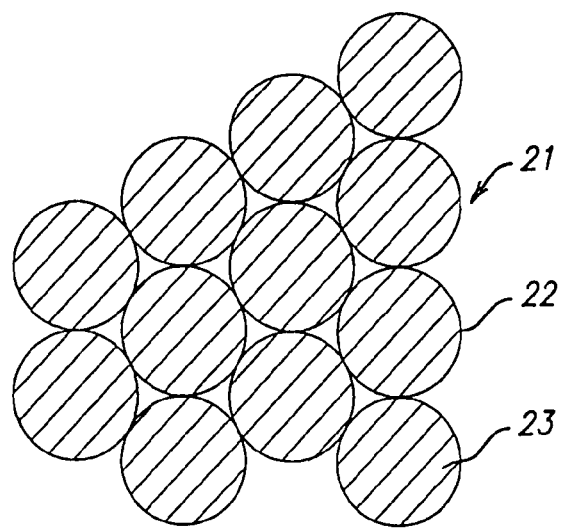
FIG. 2 Schematic illustration of normal fat cells.
Figure 3:
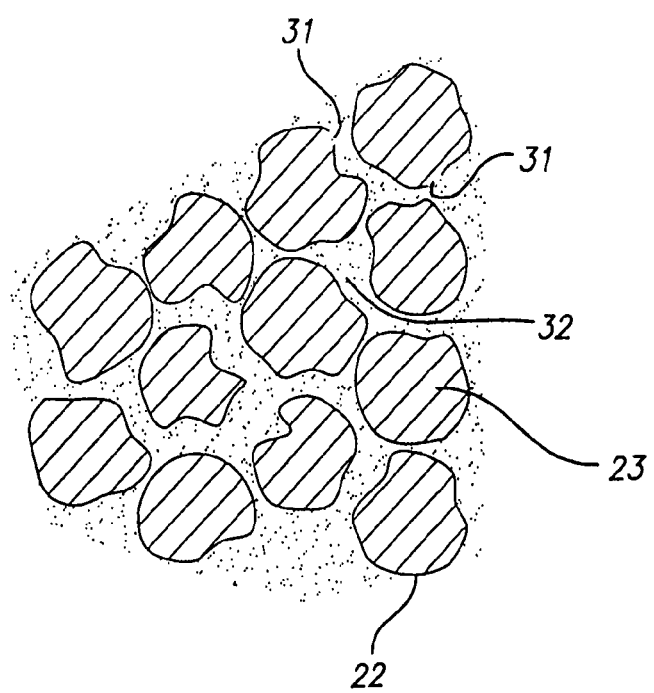
FIG. 3 Schematic illustration of fat cells after externally-applied low-level laser radiation.

The mechanism involved in releasing the intracellular fat from the cells is believed to be the formation of a transitory pore in the cell membrane. FIG. 2 illustrates adipose tissue comprising normal fat cells 21 wherein the cell membrane 22 is filled with intracellular fat 23. Upon sufficient doses of low-level laser energy, the cell membrane 22 is momentarily disrupted, releasing the intracellular fat 23. See FIG. 3, which illustrates pores 31 in the cellular membrane 22 which have released intracellular fat 23 into the interstitial space 32. Upon cessation of the energy application, the pores 31 close and the cell membrane 22 returns to contiguity. The fat cell is not destroyed, provided the duration of laser treatment is appropriate. For a 635 nm laser of less than 1 W, treatments of less than about 12 minutes do not destroy cells.

The laser energy applied is low level, that is, the treatment has a dose rate that causes no immediate detectable temperature rise of the treated tissue and no macroscopically visible changes in tissue structure. The laser energy penetrates the skin and is specific to the depth of the desired zone of fat to be treated. Consequently, the treated and surrounding tissue is not heated and is not damaged. Preferably the laser light is visible to the human eye so that the area of application is easily determined. A laser device that provides this low-level energy is known in the art as a cold laser, such as the inventions described in U.S. Pat. No. 6,013,096 issued to Tucek and U.S. Pat. No. 6,746,473, issued to Tucek and Shanks. Other lasers known in the art for use in low-level laser therapy include Helium-Neon lasers having a 632 nm wavelength and semiconductor diode lasers with a broad range of wavelengths between 405-1500 nm. The laser device may have one or more laser energy sources. Different therapy regimens require diodes of different wattages. The preferred laser diodes use less than one watt of power each to simultaneously facilitate liposuction, treat post-operative inflammation, and post-operative pain. Diodes of various other wattages may also be employed to achieve the desired laser energy for the given regimen. Low-level lasers are available commercially.

The dosage of laser energy required to achieve release of the intracellular fat into the interstitial space will vary depending on the thickness of the patient's skin, thickness of fatty tissue, and other biological factors peculiar to each patient. The following examples are illustrative:

EXAMPLE 1

A 635 nm semiconductor diode laser with maximum power of 10 mW was used to apply laser light to a patient's pads of fat located in the area near his waist, around his side and back, commonly referred to as "love handles." The laser energy was applied for 12 minutes in a back-and-forth sweeping motion across the fat areas without touching the patient. This non-invasive procedure produced the same amount of fat reduction as would be seen with an invasive procedure using tumescent solution and liposuction. The patient suffered no pain or bruising.

EXAMPLE 2

A 635 nm semiconductor diode laser with maximum power of 10 mW was used to apply laser light to a patient's pads of fat located in the area near his waist, around his side and back. The laser energy was applied in a back-and-forth sweeping motion across the fat areas without touching the patient. The patent was treated three times over a 48 hour period for 12-15 minutes per treatment. This non-invasive procedure produced the same amount of fat reduction as would be seen with an invasive procedure using tumescent solution and liposuction. The patient suffered no discomfort.

While there has been illustrated and described what is at present considered to be a preferred embodiment of the present invention, it will be understood by those skilled in the art that various changes and modifications may be made, and equivalents may be substituted for elements thereof without departing from the true scope of the invention. Therefore, it is intended that this invention not be limited to the particular embodiment disclosed as the best mode contemplated for carrying out the invention, but that the invention will include all embodiments falling within the scope of the appended claims.

We claim:

1. A method for reducing fat of a patient, wherein the fat comprises fat cells having intracellular fat and interstitial space between the fat cells, the method comprising applying monochromatic red laser energy externally to the patient in an amount that causes no detectable temperature rise of the treated tissue to release at least a portion of the intracellular fat into the interstitial space wherein the released fat is removed from the patient's body through one or more of the patient's normal bodily systems.

2. The method according to claim 1 wherein the laser energy is about 635 nm.

3. A method for reducing fat of a patient from a targeted area, the method comprising applying monochromatic red laser energy externally to the patient at the targeted area in a dose rate that causes no detectable temperature rise of the treated tissue.

4. The method according to claim 3 wherein the laser energy is about 635 nm.

5. A method for reducing fat in a targeted area of a patient's body, the method consisting of applying sufficient low-level monochromatic laser energy having a wavelength of between 630 nm and 649 nm to release the targeted area's intracellular fat into the targeted area's interstitial space without inducing a temperature rise of the tissue in the targeted area and without causing lipolysis of the fat.

6. A method for reducing fat of a patient, wherein the fat comprises fat cells having intracellular fat and interstitial space between the fat cells, the method consisting of applying unfiltered red laser energy externally to the patient in an amount that causes no detectable temperature rise of the treated tissue to release at least a portion of the intracellular fat into the interstitial space wherein the released fat is removed from the patient's body through one or more of the patient's normal bodily systems.

7. The method according to claim 6 wherein the laser energy has a wavelength of about 635 nm.

8. A method for reducing fat of a patient from a targeted area, the method comprising applying unfiltered red laser energy externally to the patient at the targeted area in a dose rate that causes no detectable temperature rise of the treated tissue.

9. The method according to claim 8 wherein the laser energy is about 635 nm.

10. A method for reducing fat in a targeted area of a patient's body, the method consisting of applying sufficient low-level unfiltered laser energy having a wavelength of between 630 nm and 649 nm to release the targeted area's intracellular fat into the targeted area's interstitial space without inducing a temperature rise of the tissue in the targeted area and without causing lipolysis of the fat.

* * * * *